(12) United States Patent
Stockholm (10) Patent No.: US 9,849,270 B2
(45) Date of Patent: Dec. 26, 2017

(54) FOLDABLE ADHESIVE COMPOSITE DRESSING

(71) Applicant: 3M INNOVATIVE PROPERTIES COMPANY, St. Paul, MN (US)

(72) Inventor: Andrew J. Stockholm, Oak Park Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 803 days.

(21) Appl. No.: 14/364,707

(22) PCT Filed: Dec. 12, 2012

(86) PCT No.: PCT/US2012/069130
§ 371 (c)(1),
(2) Date: Jun. 12, 2014

(87) PCT Pub. No.: WO2013/090353
PCT Pub. Date: Jun. 20, 2013

(65) Prior Publication Data
US 2014/0303594 A1 Oct. 9, 2014

Related U.S. Application Data

(60) Provisional application No. 61/576,507, filed on Dec. 16, 2011.

(51) Int. Cl.
*A61M 31/00* (2006.01)
*A61F 13/02* (2006.01)
(Continued)

(52) U.S. Cl.
CPC ............. *A61M 35/00* (2013.01); *A61B 18/04* (2013.01); *A61B 18/14* (2013.01); *A61K 9/0021* (2013.01);
(Continued)

(58) Field of Classification Search
CPC . A61B 18/04; A61B 18/14; A61B 2018/0047; A61B 2018/00577;
(Continued)

(56) References Cited

U.S. PATENT DOCUMENTS

| 4,472,480 | A | 9/1984 | Olson |
| 4,584,355 | A | 4/1986 | Blizzard et al. |

(Continued)

FOREIGN PATENT DOCUMENTS

| WO | WO 86/00220 | 1/1986 |
| WO | WO 2008/091878 | 7/2008 |

(Continued)

*Primary Examiner* — Jason Flick (57) ABSTRACT

An adhesive composite dressing useful for applying an active ingredient to a treated skin site, as well as methods of manufacture and use of such dressings. In one embodiment, an adhesive composite dressing comprising an anchor member, a target member, and a folding member, where the anchor member comprises a first skin-contact adhesive, the target member comprises an opening adapted to enable skin treatment, the folding member comprises a drug reservoir, and where the folding member is attached to the anchor portion through a hinge defined by a line of attachment that is not contiguous with an edge of the anchor member.

14 Claims, 5 Drawing Sheets

(51) Int. Cl.
  *A61M 35/00*  (2006.01)
  *A61K 9/70*   (2006.01)
  *A61K 9/00*   (2006.01)
  *A61B 18/04*  (2006.01)
  *A61B 18/14*  (2006.01)
  *A61M 37/00*  (2006.01)
  *A61B 18/00*  (2006.01)

(52) U.S. Cl.
  CPC ......... *A61K 9/703* (2013.01); *A61M 37/0015* (2013.01); *A61B 2018/0047* (2013.01); *A61B 2018/00577* (2013.01); *A61M 2037/0023* (2013.01); *A61M 2037/0061* (2013.01); *Y10T 156/10* (2015.01)

(58) Field of Classification Search
  CPC ........ A61K 9/0021; A61K 9/703; A61K 9/70; A61K 9/7007; A61K 9/7023; A61K 9/7038; A61K 9/7084; A61K 9/7092; A61M 2037/0023; A61M 2037/0061; A61M 35/00; A61M 37/0015; Y10T 156/10
  USPC ....................................................... 604/506
  See application file for complete search history.

(56) References Cited

U.S. PATENT DOCUMENTS

| | | |
|---|---|---|
| 4,585,836 A | 4/1986 | Homan et al. |
| 4,591,622 A | 5/1986 | Blizzard et al. |
| 4,627,429 A | 12/1986 | Tsuk |
| 4,655,767 A | 4/1987 | Woodard et al. |
| 4,693,776 A | 9/1987 | Krampe et al. |
| 4,751,087 A | 6/1988 | Wick |
| 4,834,979 A | 5/1989 | Gale |
| 5,019,034 A | 5/1991 | Weaver et al. |
| 5,223,261 A | 6/1993 | Nelson et al. |
| 5,380,760 A | 1/1995 | Wendel et al. |
| 5,531,855 A * | 7/1996 | Heinecke ............ A61F 13/0276 156/248 |
| 5,656,286 A | 8/1997 | Miranda et al. |
| 5,688,523 A | 11/1997 | Garbe et al. |
| 5,783,269 A | 7/1998 | Heilmann et al. |
| 5,885,211 A | 3/1999 | Eppstein et al. |
| 6,004,578 A | 12/1999 | Lee et al. |
| 6,024,976 A | 2/2000 | Miranda et al. |
| 6,091,975 A | 7/2000 | Daddona et al. |
| 6,129,929 A | 10/2000 | Wick |
| 6,148,232 A | 11/2000 | Avrahami |
| 6,149,935 A | 11/2000 | Chiang et al. |
| 6,173,202 B1 | 1/2001 | Eppstein |
| 6,234,990 B1 | 5/2001 | Rowe et al. |
| 6,312,612 B1 | 11/2001 | Sherman et al. |
| 6,365,178 B1 | 4/2002 | Venkateshwaran et al. |
| 6,379,324 B1 | 4/2002 | Gartstein et al. |
| 6,745,071 B1 | 6/2004 | Anderson et al. |
| 2003/0054025 A1 | 3/2003 | Cantor et al. |
| 2004/0049150 A1 | 3/2004 | Dalton et al. |
| 2004/0202708 A1 | 10/2004 | Roehrig et al. |
| 2005/0261631 A1 | 11/2005 | Clarke et al. |
| 2006/0047242 A1* | 3/2006 | Laurent ................ A61B 17/205 604/46 |
| 2008/0262284 A1 | 10/2008 | Marcenyac et al. |
| 2008/0274146 A1 | 11/2008 | Bartholomaus et al. |
| 2008/0274166 A1* | 11/2008 | Sacks .................. A61K 9/7084 424/449 |
| 2010/0286588 A1* | 11/2010 | Bar-El ................. A61N 1/0424 604/20 |

FOREIGN PATENT DOCUMENTS

| | | |
|---|---|---|
| WO | WO 2009/047774 | 4/2009 |
| WO | WO 2011/066493 | 6/2011 |

* cited by examiner

FOLDABLE ADHESIVE COMPOSITE DRESSING

CROSS REFERENCE TO RELATED APPLICATIONS

This application is a national stage filing under 35 U.S.C. 371 of PCT/US2012/069130, filed Dec. 12, 2012, which claims priority to U.S. Provisional Patent Application No. 61/576,507, filed Dec. 16, 2011, the disclosure of which is incorporated by reference in its entirety herein.

FIELD

The present disclosure relates to adhesive composite dressings that can be used to apply an active ingredient to a treated skin site, as well as methods of manufacturing and using such adhesive composite dressings.

BACKGROUND

Transdermal and topical drug delivery can be used for therapeutic treatment, but the number of molecules that can be effectively delivered using these routes can be limited by the barrier properties of skin.

A number of different skin treatment methods have been proposed in order to increase the permeability or porosity of the outermost skin layers, thus enhancing drug delivery through or into those layers. Among these methods are microneedles, laser ablation, RF ablation, heat ablation, sonophoresis, and iontophoresis.

In some cases, these treatments are provided by a single integrated device that performs two separate functions: the device treats the skin and also delivers an active ingredient to the treated skin. An example would be a hollow microneedle array with an attached drug reservoir. The microneedles pierce the skin and remain attached while the drug flows from the reservoir into the skin. Although devices of this type may be conceptually easy for a patient to administer, they can be complex and/or limited in the amount of drug they can effectively deliver.

Alternatively, a treatment device can be used in a first step to perform the function of treating the skin to increase permeability and/or create pores. The treatment device is then removed and, in a second step, a separate drug reservoir (e.g., a cream, solution, or patch) is placed on the treated skin area to perform the second function of delivering the active ingredient to the treated skin. Although this includes an additional user step, the separation of skin treatment from drug delivery can afford simplicity in device design, as well as providing flexibility in the design to better match the specific needs of these two different functions.

BRIEF SUMMARY

The present disclosure relates to adhesive composite dressings that can be used to apply an active ingredient to a treated skin site, as well as methods of manufacturing and using such dressings. A feature and advantage of embodiments of the present disclosure is that they can ensure that the drug reservoir is accurately aligned with the treated area on the skin, as the typical skin treatments are microscopic in nature and thus the treated skin will generally not have a different appearance from untreated skin.

Further features and advantages of embodiments of this disclosure will be understood upon consideration of the detailed description, as well as the appended claims. These and other features and advantages of the embodiments of this disclosure may be described below. The above summary is not intended to describe each embodiment or every implementation of the present disclosure.

The subject matter of this disclosure, in its various combinations, either in apparatus or method form, may include the following list of embodiments:

1. An adhesive composite dressing comprising an anchor member, a target member, and a folding member,
   the anchor member comprising a first skin-contact adhesive,
   the target member comprising an opening adapted to enable skin treatment
   the folding member comprising a drug reservoir,
   wherein the folding member is attached to the anchor portion through a hinge defined by a line of attachment that is not contiguous with an edge of the anchor member.

2. The adhesive composite dressing of embodiment 1 wherein the folding member is attached to the anchor member by an adhesive layer.

3. The adhesive composite dressing of embodiments 1 or 2 wherein the folding member further comprises a second skin-contact adhesive.

4. The adhesive composite dressing of embodiment 3 wherein the dressing further comprises a support layer releasably attached to the folding member on the side opposed to the second skin-contact adhesive.

5. The adhesive composite dressing of embodiments 3 or 4 wherein the dressing further comprises an impermeable barrier between the drug reservoir and the second skin-contact adhesive.

6. The adhesive composite dressing of any one of the preceding embodiments wherein the drug reservoir and the target member opening are positioned opposed to each other and equidistant from the hinge so that the drug reservoir may come into alignment with a treated area of skin when the folding member is folded so as to be adjacent to the treated area of skin.

7. The adhesive composite dressing of any one of the preceding embodiments, wherein the dressing is adapted to be connected to a skin treatment device.

8. The adhesive composite dressing of embodiment 7 wherein the dressing is adapted to be releasably connected to the skin treatment device by an adhesive, mechanically, or by magnetic force.

9. The adhesive composite dressing of embodiments 7 or 8 wherein the skin treatment device is selected from the group consisting of an RF ablation device, a heat ablation device, and a microneedle array.

10. The adhesive composite dressing of any one of the preceding embodiments wherein the drug reservoir comprises a drug selected from the group consisting of proteins, peptides, nucleotide sequences, monoclonal antibodies, vaccines, polysaccharides, and antibiotics.

11. The adhesive composite dressing of any one of the preceding embodiments wherein the dressing is provided within a hermetically sealed pouch.

12. An adhesive composite dressing having a plurality of flat layers laminated in a stack wherein at least one layer defines a target opening and at least one layer defines a drug reservoir, wherein the relative alignment of at least two of the layers defines an adhered and non-adhered region between the at least two layers so as to define a hinge, wherein the drug reservoir and target opening are positioned so that when the drug reservoir is folded about the hinge it aligns with the target opening, and wherein the patch is configured so that it may be prepared and initially applied to a skin surface without folding any of the individual flat layers.

13. A kit comprising an adhesive composite dressing of any one of the preceding embodiments and a skin treatment device.

14. The kit of embodiment 13 wherein the adhesive composite dressing is releasably attached to the skin treatment device.

15. A method of applying a drug reservoir to a treated area of skin with a patch having an anchor member, a target member, and a folding member, the folding member comprising the drug reservoir and being attached to the anchor portion through a hinge defined by a line of attachment that is not contiguous with an edge of the anchor member, the target member comprising an opening adapted to enable skin treatment, the method comprising:
  a) attaching the anchor member of the patch to a non-treated area of skin,
  b) treating the area of skin left exposed by the target opening with a treatment method that increases the permeability of the skin, and
  c) rotating the folding member around the hinge so that at least a portion of the folding member adheres to the skin and so that the drug reservoir contacts the treated area of skin.

16. The method of embodiment 15 wherein the skin is treated with a skin treatment device selected from the group consisting of an RF ablation device, a heat ablation device, and a microneedle array.

17. The method of embodiments 15 or 16 further comprising the step of removing the anchor member from the skin while leaving the drug reservoir in contact with the treated area of skin.

18. The method of any one of embodiments 15 to 17 wherein the increased permeability of the skin is with respect to pharmaceutically active agents.

19. The method of any one of embodiments 15 to 18 wherein the treatment method forms a plurality of pores in the skin.

20. A method of manufacturing an adhesive composite dressing according to embodiment 12 wherein the flat layers are laminated using rotary processing equipment.

BRIEF DESCRIPTION OF THE DRAWINGS

The disclosure may be more completely understood in consideration of the following detailed description of various embodiments of the disclosure in connection with the accompanying drawings, in which.

Those skilled in the art will recognize that the figures are not necessarily to scale. Like numbers used in the figures generally refer to like components, although those skilled in the art will recognize that the use of a number to refer to a component in a given figure does not limit the component in another figure labeled with the same number.

DETAILED DESCRIPTION OF THE DRAWINGS

In the following detailed description, reference is made to the accompanying drawings that form a part of the present disclosure, and in which are shown by way of illustration only several specific embodiments. Those skilled in the art will recognize that other embodiments are contemplated and may be made without departing from the scope or spirit of the present disclosure. The following detailed description, therefore, is not to be taken in a limiting sense.

The scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Figure 1:
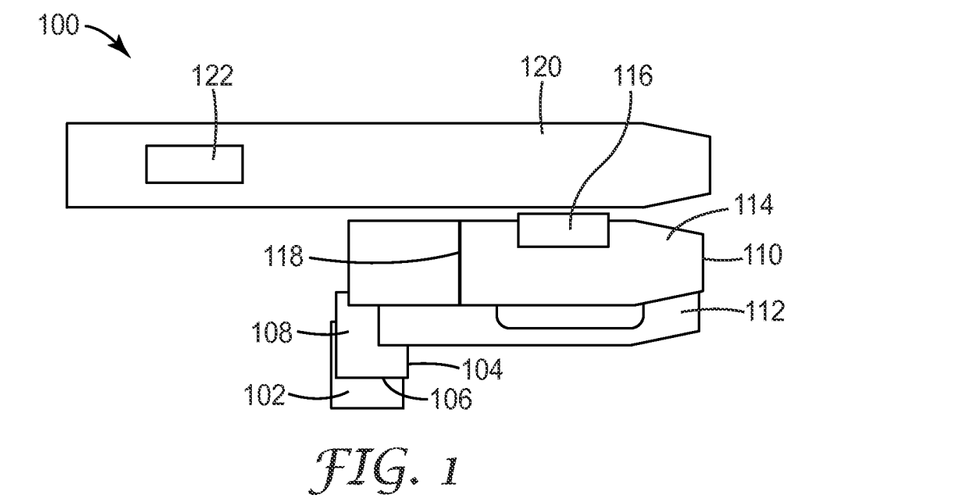
FIG. 1 is a schematic exploded top perspective view of an adhesive composite dressing according to embodiments of the present disclosure.
Figure 2:
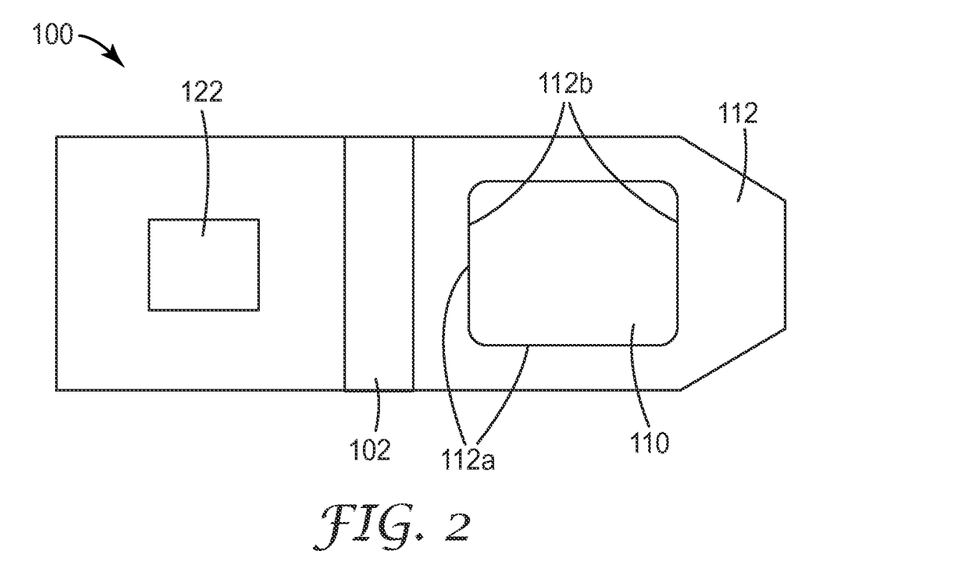
FIG. 2 is a schematic top plan view of the adhesive composite dressing of FIG. 1.
Figure 3A:
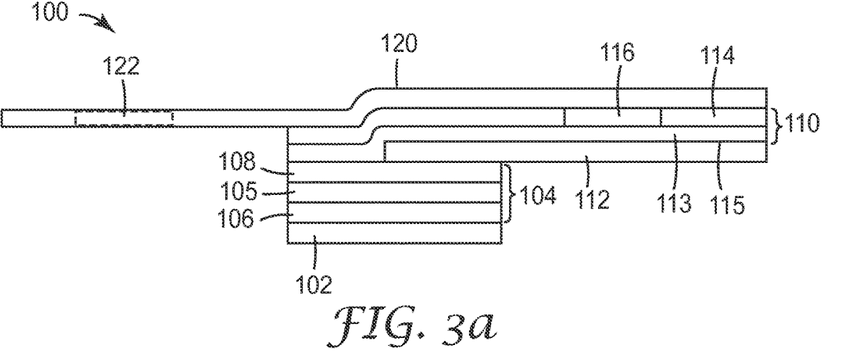
FIG. 3A is a schematic cross-sectional view of a first embodiment of an adhesive composite dressing.

FIG. 1 is an exploded perspective view of embodiments of an adhesive composite dressing 100 of the present disclosure. The dressing comprises a tape, such as a double-coated tape 104, which can serve as an anchor member. On one side of the double coated tape 104 can be a skin-contact adhesive 106 that can be suitable for applying to the skin of a patient. Prior to use, the skin-contact adhesive 106 can be protected by a removable release liner 102. On the other side of the double coated tape 104 can be an adhesive layer 108 that can be suitable for use in a medical dressing, but it is not necessary that the adhesive layer 108 be a skin-contact adhesive. The adhesive layer 108 may optionally be of the same composition and construction as skin-contact adhesive 106. As shown in detail in FIG. 3A, the double coated tape 104 can have a backing layer 105 that supports skin-contact adhesive layer 106 and adhesive layer 108. The adhesive layer 108 can be adhered to a portion of the backing 113 of an adhesive dressing 110 through a generally relatively strong, which can be permanent, adhesive bond. The adhesive dressing 110 can have a supporting carrier 112 removably attached to and covering a portion of the backing 113. The side of the carrier 112 opposed to the backing 113 of the adhesive dressing 110 can be a low energy surface that does not bond to or only generally relatively weakly and removably bonds to the adhesive layer 108 of the double coated tape 104. As depicted, about half of the adhesive layer 108 can be strongly, optionally permanently, bonded to the adhesive dressing 110 and about half of the adhesive layer 108 can be not bonded or only generally relatively weakly bonded to the carrier 112. This partial adhesion enables the adhesive dressing 110 to act as a folding member as further described below.

Figure 3B:
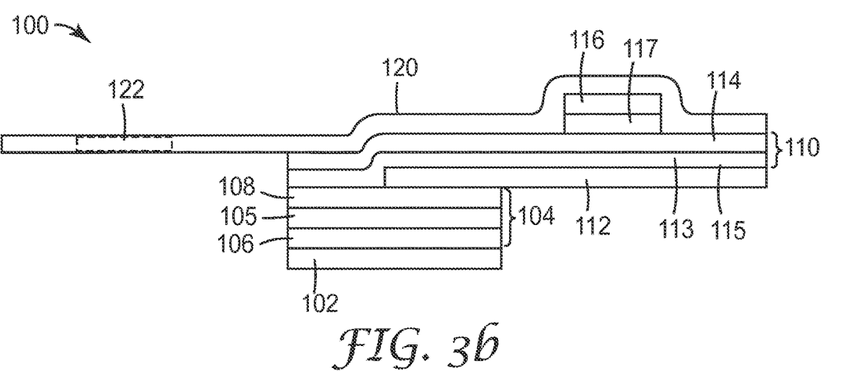
FIG. 3B is a schematic cross-sectional view of a second embodiment of an adhesive composite dressing.

The adhesive dressing 110 can have a pressure sensitive adhesive 114, which can be a skin-contact adhesive, disposed on the backing 113 and a drug reservoir 116 further disposed on or in a portion of the pressure sensitive adhesive 114 thereby forming a medicated portion of the adhesive dressing. The medicated portion may extend across the entire adhesive dressing, but can be limited to a smaller medicated zone approximately in the center of the dressing. The drug reservoir 116 may be formed on the dressing in a number of different ways. For example, the drug may be directly mixed or infused with a portion of the pressure sensitive adhesive 114. Alternatively, the drug may be present as a powder adhered to a portion of the surface of the skin-contact adhesive. Alternatively, the drug may be embedded in a polymeric matrix that can be adhered to the pressure sensitive adhesive 114. The drug-containing polymeric matrix may further optionally have a drug reservoir backing layer 117 that inhibits direct contact between the drug-containing polymeric matrix and the pressure sensitive adhesive 114, as shown in FIG. 3B. As will be described below, the adhesive dressing 110 may optionally have a perforation 118 that permits the adhesive dressing to be divided into two portions.

Prior to use, the pressure sensitive adhesive 114 and drug reservoir 116 can be protected by a liner 120. The liner 120 can be removably adhered to the pressure sensitive adhesive 114 and optionally to the drug reservoir 116 (in embodiments where the drug reservoir 116 or matrix it is embedded it can have adhesive properties). The liner 120 covers and protects both pressure sensitive adhesive 114 and drug reservoir 116. A portion of the liner 120 extends beyond the adhesive dressing. This portion includes a target opening 122 that can be spaced precisely in relation to the drug reservoir 116 so as to define a target area on the skin of a subject which can come into contact with the drug reservoir 116 as further described below. As shown, the target opening 122 is rectangular, but those skilled in the art will recognize that any suitable shape, such as a circle, oval, hexagon, or the like, may be used. In general, the target opening can be sized and shaped so as to enable accurate alignment of a treatment device. As such, it may also include one or more asymmetric features, such as notches or protrusions that aid in aligning the treatment device. The target opening may also be surrounded by one or more guiding marks, such as lines or arrows that aid in the placement of the treatment device with respect to the target opening. In one embodiment, the treated area of skin 132 will correspond directly to the size of the target opening 122. In an alternate embodiment, the treated area of skin 132 will be smaller than the target opening 122.

Figure 4A:
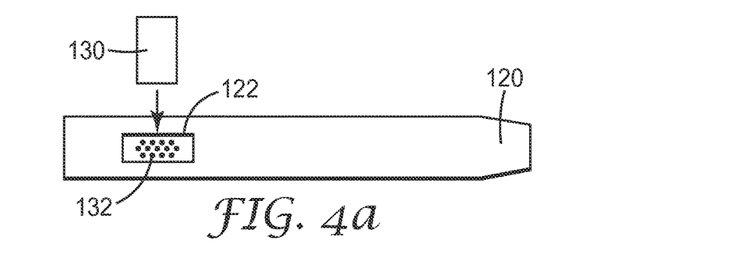
FIGS. 4A-4G are schematic perspective views illustrating use of an adhesive composite dressing according to embodiments of the present disclosure.
Figure 4B:
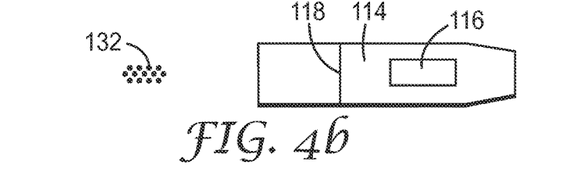
Figure 4C:
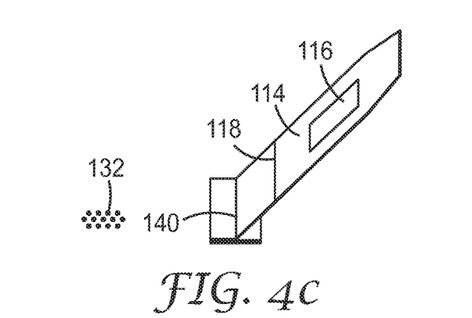
Figure 4D:
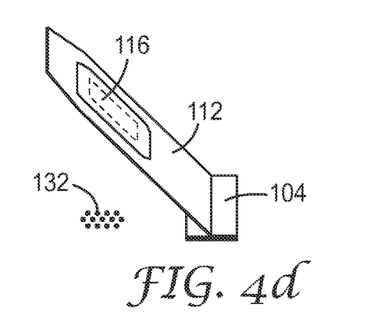
Figure 4E:
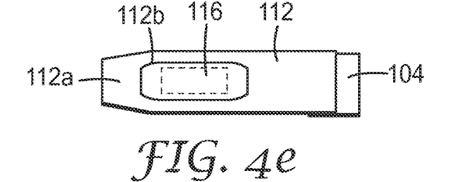
Figure 4F:
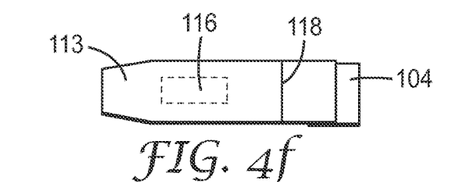
Figure 4G:
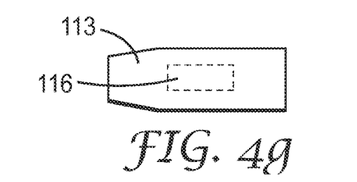

In use, the release liner 102 of adhesive composite dressing 100 can be removed from the skin-contact adhesive 106. The skin-contact adhesive 106 can be adhered or anchored to a skin surface so as to align the target opening 122 with a desired area of skin. As shown in FIG. 4A, a skin treatment device 130, such as a microneedle array, abrader, microporator, sonophoresis device, or the like, can be used to treat an area of skin 132 left exposed by the target opening 122. The treated area of skin 132 is shown as a pattern of dots in FIGS. 4A-D, which could, for instance, correspond to a pattern of discrete pores formed by a microporator or a microneedle array, but it should be understood that this is schematic in nature and that the treated skin could be uniformly treated, as by an abrader, or in any number of different patterns of increased permeability of the treated skin. Following skin treatment, the liner 120 can be removed from the adhesive dressing 110, as shown in FIG. 4B. The edge of the adhesive dressing 110 and carrier 112 distal from the anchored portion can be grasped and rotated around the hinge 140 formed by the partial adherence of the backing side of an adhesive dressing 110 to the double coated tape 104 as shown in FIGS. 4C-E until the pressure sensitive adhesive 114 of the adhesive dressing 110 can be adhered to the skin. It can be seen that accurate alignment of the target opening 122 and the drug reservoir 116 with respect to the hinge 140 enables the drug reservoir 116 to align with the treated area of skin 132. In addition, the hinge 140 can be formed along a line that approximately bisects the anchor member. More generally, it can be desirable that the hinge is not formed contiguous with an edge of the anchor member, as this can reduce the likelihood that the anchor member might inadvertently lift from the skin while the adhesive dressing is being rotated from its initial position towards its ultimate attachment to the treated skin area. Once the adhesive dressing is applied to the treated skin area, the carrier 112 may be optionally removed from the adhered dressing, as shown in FIG. 4F. In a further step, the double coated tape 104 anchor and a portion of the adhesive dressing 110 may also be optionally removed using the perforation 118 in order to leave a smaller adhered dressing, as shown in FIG. 4G. The skin-contact adhesive 106 of the anchor member may be optimized for short time of wear in embodiments where the anchor member is separated from the dressing and removed from the skin just after application. For example, it may be desired to make the skin-contact adhesive 106 have relatively weak adhesion so as to make it easy to remove. Alternatively, adhesives that have a tendency to flow or ooze over time may be suitable for use as skin-contact adhesive 106, as they would only be applied to the skin for a short time.

In embodiments, the liner 120 and target opening 122 may be configured so as to be coupled to the skin treatment device 130. For example, the skin treatment device may have a slot that enables the liner 120 to be inserted into the treatment device so as to properly align the target opening 122 with the part of the treatment device that treats skin. Alternatively, the liner 120 may be temporarily adhered to the underside of the skin treatment device 130 or releasably connected by magnetic force. Alternatively, the liner 120 may be temporarily mechanically attached to the skin treatment device 130. In one embodiment, the liner 120 may comprise a disposable treatment device, such as a microneedle array, aligned with the target opening 122. In such an instance, the microneedle array would be inserted into the skin to treat the skin surface prior to being removed along with the liner 120. Although not described in greater detail, it should be apparent to one of ordinary skill in the art that additional attachment members could be used to attach the treatment device to the liner 120 and that additional protective layers, such as a protective cover for a microneedle array, might be employed as necessary. In one embodiment, the dressing may make up part of a kit containing the dressing along with a skin treatment device. The dressing and skin treatment device may be provided separately within the kit or they may be attached to each other within the kit.

As shown in FIGS. 1-4, a carrier 112 is used to both help define a hinge 140 and to support the adhesive dressing 110 as it is rotated about the hinge 140 and adhered to the skin. This support of the dressing can be particularly important where the dressing is formed of a very thin and highly conformable layer. In one embodiment the adhesive dressing 110 will comprise a backing layer with sufficient rigidity so as not to need a carrier 112 for support. In such an embodiment, however, it can still be necessary to ensure that a portion of the double coated tape 104 adhesive layer 108 does not adhere to the adhesive dressing 110. As will be readily apparent, this may be accomplished in a number of ways. For example, a piece of non-adhesive film may be used to cover the part of the adhesive layer 108 that would have otherwise have been covered by the carrier 112. Alternatively, a strip on the back side of the adhesive dressing 110 may be coated with a low-energy or release material, such that the low-energy strip removably adheres to the adhesive layer 108, but the remainder of the bond between adhesive dressing 110 and adhesive layer 108 remains strong enough to form a hinge. In still another alternative, the double coated tape 104 can be coated in a stripe-coating process, such that the adhesive layer 108 only covers a portion of the double coated tape 104 surface, as shown in FIG. 3C. It should also be appreciated that the foregoing alternatives could also be used with embodiments having a carrier 112.

As shown in FIGS. 1-4, the anchor member can be formed from a double-coated tape, with the skin-contact adhesive serving to anchor it to the skin. Alternatively, the double coated tape 104 may be replaced by a single-coated tape having only a skin-contact adhesive 106. The adhesive dressing 110 will then be attached to the backing of the single-coated tape, for example, through an adhesive strip on the underside of the adhesive dressing or by directly welding the backing side of the adhesive dressing to the single-coated tape. In general, it should be appreciated that the precise nature of the attachment between adhesive dressing and anchor member is not critical, so long as it enables formation of a hinge that enables accurate alignment of drug reservoir and target opening during use.

As shown in FIGS. 1-4, the anchor member can be a relatively narrow rectangle or strip. Alternatively, the anchor member may extend further below either the carrier 112 or the liner 120 so as to better support the patch when it is applied to the skin. In particular, it may be desirable to have the anchor member extend below the liner 120 with an opening in the anchor member aligned with the target opening 122. In such a manner, the liner 120 and target opening 122 would be held in place against the skin by the anchor member adhesive, thus aiding in the precise alignment of the target opening 122 relative to the adhesive dressing 110.

As shown in FIGS. 1-4, one embodiment is a patch having a plurality of flat layers laminated in a stack wherein at least one layer defines a target opening 122 and at least one layer defines a drug reservoir 116. The relative alignment of the adhesive dressing 110, carrier 112, and the double coated tape 104 defines an adhered and non-adhered region between the adhesive dressing 110 and the double coated tape 104 so as to define a hinge 140. The drug reservoir 116 and target opening can be positioned so that when the drug reservoir 116 is folded about the hinge 140 it aligns with the area on the skin that was initially aligned with the target opening 122. The patch can be configured so that it may be prepared and initially applied to a skin surface without folding any of the individual flat layers. It should be appreciated that this represents a manufacturing advantage, as preparation and lamination of flat films or tapes is a well-known and economic process that may be done with a high degree of precision. Once prepared and applied to the skin, it is then the relative alignment of the various flat layers that enables the overall patch to accurately fold about a hinge, thus removing any necessity of attempting to accurately fold layers during manufacture, as well as the necessity of retaining such folds prior to use. In FIGS. 3A and 3B the adhesive dressing 110 and liner 120 each can have a small ridge in the center and likewise in FIG. 3B the liner 120 has two additional ridges surrounding the drug reservoir 116, but it should be noted these ridges are greatly magnified in the schematic views in order to distinguish the different layers. The thicknesses of the carrier 112, the drug reservoir 116 and the drug reservoir backing layer 117 can be on the order of 25 to 100 microns (984.3 to 3937 microinches), so in practice, the layers depicted with ridges lay entirely flat or essentially entirely flat.

In one embodiment, the patch may be constructed from easily constructed individual components, thus enabling ease of manufacture. For instance, the anchor member may be a conventional strip of double-coated tape protected on one side by a release liner. The adhesive dressing may be a conventional transparent dressing that is modified by removing a strip along one side of the carrier to enable the proper hinge construction as described above. The drug reservoir may be a conventional transdermal patch or have the same construction as a conventional transdermal patch. The top release liner may be a conventional liner die cut to provide a target opening and the appropriate shape to protect the adhesive dressing. These four components may then be combined in series by aligning and adhering each component in turn. That is, the adhesive dressing can be aligned and adhered to the double-coated tape. Next, the drug reservoir can be aligned and adhered to the adhesive dressing. Finally, the top release liner can be aligned and adhered to the adhesive dressing/drug reservoir combination.

Skin-contact adhesive layers will generally be selected according to the desired end use of the dressings. Where the dressing comprises more than one skin-contact adhesive layer, each skin-contact adhesive layer may be selected independently of each other with regard to material and thickness used. Examples of suitable adhesives include acrylates, silicones, polyisobutylenes, synthetic rubber, natural rubber, and copolymers and mixtures thereof. Acrylates and silicones can be preferred skin-contact adhesive layers. In general, the skin-contact adhesive should cause little or no irritation or sensitization of the skin during the intended wear period.

In one embodiment the skin-contact adhesive can be an acrylate (or methacrylate) copolymer. Acrylates will typically have an inherent viscosity greater than about 0.2 dL/g and will comprise one or more polymerized primary monomers and optionally one or more polar comonomers. Primary monomers suitable for use include alkyl acrylates containing 4 to 12 carbon atoms in the alkyl group and alkyl methacrylates containing 4 to 12 carbon atoms in the alkyl group. Examples of suitable alkyl acrylates and methacrylates include n-butyl, n-pentyl, n-hexyl, isoheptyl, n-nonyl, n-decyl, isohexyl, 2-ethyloctyl, isooctyl and 2-ethylhexyl acrylates and methacrylates. In embodiments, preferred alkyl acrylates include isooctyl acrylate, 2-ethylhexyl acrylate, n-butyl acrylate, and cyclohexyl acrylate. Polar monomers suitable for use include those having hydroxyl, amide, or carboxylic, sulfonic, or phosphonic acid functionality. Representative examples include acrylamide, methacrylamide, N-vinyl-2-pyrrolidone, 2-hydroxyethylacrylate, 2-hydroxyethylmethacrylate, hydroxypropylacrylate, acrylic acid, methacrylic acid, pyrrolidonyl ethyl acrylate, and alkoxyethyl acrylates, such as 2-carboxyethylacrylate. In some embodiments, the amount by weight of polar monomer will not exceed about 40% of the total weight of all monomers in order to avoid excessive firmness of the final PSA product. Typically, polar monomer can be incorporated to the extent of about 1% to about 20% by weight. In one embodiment the polar monomer can be acrylamide.

In some embodiments, the acrylate copolymer can comprise the reaction product of primary and polar monomers and additional optional monomers which, when present, are included in the polymerization reaction in quantities that will not render the adhesive composition non-tacky. The optional additional monomers may be added, for example, to improve performance, reduce cost, or for other purposes. Examples of such optional monomers include vinyl esters, such as vinyl acetate, vinyl chloride, vinylidene chloride, styrene, and macromonomers copolymerizable with the other monomers. Suitable macromonomers include polymethylmethacrylate, styrene/acrylonitrile copolymer, polyether, and polystyrene macromonomers. Examples of useful macromonomers and their preparation are described in U.S. Pat. No. 4,693,776 (Krampe et al.), the disclosure of which is incorporated herein by reference Silicone or polysiloxane pressure-sensitive adhesives include pressure-sensitive adhesives which are based on two major components: a polymer, or gum, and a tackifying resin. The polysiloxane adhesive can be prepared by cross-linking the gum, typically a high molecular weight polydiorganosiloxane, with the resin, to produce a three-dimensional silicate structure, via a condensation reaction in an appropriate organic solvent. The ratio of resin to polymer can be adjusted in order to modify the physical properties of polysiloxane adhesives. Use of capped (or amine-compatible) polysiloxanes can, in embodiments, be preferred so as to increase drug stability and reduce degradation. Further details and examples of silicone pressure-sensitive adhesives which can be useful are described in the U.S. Pat. No. 4,591,622 (Blizzard et al.); U.S. Pat. No. 4,584,355 (Blizzard et al.); U.S. Pat. No. 4,585,836 (Homan et al.); and U.S. Pat. No. 4,655,767 (Woodard et al.). Suitable silicone pressure-sensitive adhesives are commercially available and include the silicone adhesives sold under the trademarks BIO-PSA® by Dow Corning Corporation, Medical Products, Midland, Mich.

Further description of suitable adhesives may be found in U.S. Pat. No. 5,656,286 (Miranda et al.), U.S. Pat. No. 5,223,261 (Nelson et al.), and U.S. Pat. No. 5,380,760 (Wendel et al.) the disclosures of which are incorporated herein by reference. In one embodiment, the skin-contact adhesive layer thickness can be more than 10 μm, often more than 20 μm, and sometimes more than 40 μm. In another embodiment, the adhesive layer thickness can be less than 2 mm (0.07874 inch), often less than 1 mm (0.03937 inch), and sometimes less than 150 microns (5906 microinches).

Some embodiments also employ an adhesive layer to bond the anchor member to the folding member. This adhesive layer may be selected from any of the adhesives described above as skin-contact adhesives. In addition, adhesives that may not be suitable for direct contact with skin may still be suitable for use as the bonding layer within the dressing.

Typical examples of flexible films employed as conventional tape backings which may be useful as a backing layer for the adhesive dressing include those made from polymer films such as polypropylene; polyethylene, particularly low density polyethylene, linear low density polyethylene, metallocene polyethylenes, and high density polyethylene; polyvinyl chloride; polyester (e.g., polyethylene terephthalate); polyvinylidene chloride; ethylene-vinyl acetate (EVA) copolymer; polyurethane; cellulose acetate; and ethyl cellulose. Coextruded multilayer polymeric films can also be suitable, such as those described in U.S. Pat. No. 5,783,269 (Heilmann et al.), the disclosure of which is incorporated herein by reference. Backings that are layered such as polyethylene terephthalate-aluminum-polyethylene composites and polyethylene terephthalate-EVA composites can also be suitable. Foam tape backings, such as closed cell polyolefin films used in 3M™ 1777 Foam Tape and 3M™ 1779 Foam Tape (available from 3M Company, St. Paul, Minn.) can also be suitable. Polyethylenes, polyethylene blends, polyethylene composites, and polyurethanes can be preferred polymer films. Polyethylenes and polyurethanes can be optimal polymer films. In one embodiment, the backing layer can be a translucent or transparent film. Additives may also be added to films used as a backing layer, such as tackifiers, plasticizers, colorants, and anti-oxidants.

The carrier material used to supply the carriers for dressings manufactured according to the present disclosure can be substantially more rigid than the backing to inhibit the backing from wrinkling during application. The carrier material can also be heat-sealable to the backing, with or without the low adhesion coating described below, for the purpose of manufacturing the dressings according to embodiments. In general, carrier materials can include, but are not limited to, polyethylene/vinyl acetate copolymer-coated papers and polyester films. One example of a carrier material is a polyethylene/vinyl acetate copolymer-coated super calendared Kraft paper (1-80BKG-157 PE; Loparex of Willowbrook, Ill.).

The dressings of the present disclosure may also include a low adhesion coating on a top face of the backing to aid in removal of the carrier. One example of a suitable low adhesion coating is coated as a solution of polyvinyl N-octadecyl carbamate and a blend of silicone resins, as described in U.S. Pat. No. 5,531,855 (Heinecke et al.), the disclosure of which is incorporated herein by reference. While top face of the adhesive dressings of the present disclosure can include a low adhesion coating, adhesive dressings without such a coating are also considered to be within the scope of the present disclosure.

In one embodiment, the backing film thickness can be more than 10 μm, often more than 20 μm, and sometimes more than 40 μm. In another embodiment, the backing film thickness can be less than 2 mm (0.07874 inch), often less than 1 mm (0.03937 inch), and sometimes less than 150 microns (5906 microinches).

In one embodiment, the adhesive layer thickness can be more than 10 μm, often more than 20 μm, and sometimes more than 40 μm. In another embodiment, the adhesive layer thickness can be less than 2 mm (0.07874 inch), often less than 1 mm (0.03937 inch), and sometimes less than 150 microns (5906 microinches).

Exemplary pharmaceutically active agents (also referred to as "drugs") that can be included in the reservoir are capable of local or systemic effect when administered to the skin. Some examples include clonidine, estradiol, nicotine, nitroglycerine, scopolamine, and fentanyl, which are commercially available in the form of transdermal devices. Other examples include antiinflammatory drugs, both steroidal (e.g., hydrocortisone, prednisolone, triamcinolone) and non-steroidal (e.g., naproxen, piroxicam, diclofenac); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone, testosterone, estradiol); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-c]quinolin-1-yl)butyl]methanesulfonamide, and acyclovir); local anesthetics (e.g., benzocaine, propofol, lidocaine, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, buprenorphine, fentanyl citrate, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatripan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; hemostatics; antiobesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, pegylated interferon-alpha); and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

In one embodiment, drugs that are of a large molecular weight may be delivered transdermally. Increasing molecular weight of a drug typically causes a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include flu vaccine, Lyme disease vaccine, rabies vaccine, measles vaccine, mumps vaccine, chicken pox vaccine, small pox vaccine, hepatitis vaccine, pertussis vaccine, rubella vaccine, diphtheria vaccine, encephalitis vaccine, yellow fever vaccine, recombinant protein vaccine, DNA vaccines, polio vaccine, therapeutic cancer vaccine, herpes vaccine, pneumococcal vaccine, meningitis vaccine, whooping cough vaccine, tetanus vaccine, typhoid fever vaccine, cholera vaccine, tuberculosis vaccine, and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in United States Patent Application Publication No. 2004/0049150 (Dalton et al.), the disclosure of which is hereby incorporated by reference.

In another embodiment, small-molecule drugs that are otherwise difficult or impossible to deliver by passive transdermal delivery may be used. Examples of such molecules include salt forms; ionic molecules, such as bisphosphonates, including sodium alendronate or pamedronate; and molecules with physicochemical properties that are not conducive to passive transdermal delivery.

The size of the drug reservoir will be suitable to deliver a selected amount of drug through the skin. Generally, the reservoir will have a surface area greater than about 0.5 cm$^2$, often greater than about 1.0 cm$^2$, and sometimes greater than about 5 cm$^2$. Generally, the reservoir will have a surface area of less than about 100 cm$^2$, and sometimes less than about 40 cm$^2$. The reservoir may have the same surface area as the adhesive dressing, but it will typically be smaller in surface area than the adhesive dressing. In embodiments, the reservoir will be centrally placed within the adhesive dressing, such that it can be surrounded on all sides by a rim of skin-contact adhesive that can help to secure the drug reservoir in place on a skin surface. The thickness of the drug reservoir will typically be more than 10 µm, often more than 20 µm, and sometimes more than 40 µm. In another embodiment, the drug reservoir thickness can be less than 2 mm (0.07874 inch), often less than 1 mm (0.03937 inch), and sometimes less than 150 microns (5906 microinches).

In some embodiments, the drug reservoir can be provided in the form of a transdermal patch adhered to the skin-contact adhesive of the dressing. Any transdermal patch suitable for the continuous transdermal delivery of a therapeutically effective amount of an appropriate medicament may be used. Suitable transdermal patches include gelled or liquid reservoirs, such as in U.S. Pat. No. 4,834,979 (Gale), so-called "reservoir" patches; patches containing matrix reservoirs attached to the skin by an adjacent adhesive layer, such as in U.S. Pat. No. 6,004,578 (Lee et al.), so-called "matrix" patches; and patches containing PSA reservoirs, such as in U.S. Pat. No. 6,365,178 (Venkateshwaran et al.), U.S. Pat. No. 6,024,976 (Miranda et al.), U.S. Pat. No. 4,751,087 (Wick) and U.S. Pat. No. 6,149,935 (Chiang et al.), so-called "drug-in-adhesive" patches, the disclosures of which are hereby incorporated by reference. In embodiments, the reservoir will have an impermeable backing that substantially or fully inhibits migration of drug and/or excipients from the reservoir into the skin-contact adhesive of the dressing. Selection of an appropriate impermeable backing will depend upon the composition of the reservoir and one skilled in the art may readily determine a suitable backing by testing dressings for drug and/or excipient migration. Typical impermeable barriers include films containing one or more polyethylene terephthalate layers and/or an aluminum barrier layer. In one embodiment, the impermeable backing can function to limit oxygen and/or water vapor permeation. Examples of impermeable backings include films having plasma-deposited amorphous glass layers, such as described in WO 2011/066493 (Kluge et al. to 3M), and films having translucent inorganic barrier layers, such as described in U.S. Patent Application Publication No. 2004/202708 (Roehrig et al. to 3M).

In another embodiment, the drug reservoir can be provided in the form of a matrix layer containing drug, the matrix layer being adhered to the skin-contact adhesive of the dressing. Such a matrix may be an adhesive layer, as described above. Alternatively the matrix layer may be non-adhesive or weakly adhesive and rely upon the surrounding rim of skin-contact adhesive on the adhesive dressing to secure the patch in place and keep the drug reservoir in contact with the skin surface.

In another embodiment, the drug reservoir can be provided in the form of solid particles embedded on the surface or within the skin-contact adhesive of the adhesive dressing. In particular, these particles may be hydrophilic, so that contact with aqueous fluid exposed at the surface of the treated skin will cause them to dissolve or disintegrate, thus releasing drug into the skin.

In another embodiment, the drug reservoir can be provided within the skin-contact adhesive of the adhesive dressing. The drug may be mixed with the skin-contact adhesive prior to forming the adhesive dressing or it may be applied to the skin-contact adhesive of the adhesive dressing in a separate process step. Examples of suitable methods for applying drug to an adhesive layer may be found in U.S. Patent Application Publication No. 2003/054025 (Cantor et al.) and U.S. Pat. No. 5,688,523 (Garbe et al.), the disclosures of which are hereby incorporated by reference.

Release liners are available from a variety of manufacturers in a wide variety of proprietary formulations. Those skilled in the art will normally test those liners in simulated use conditions against an adhesive of choice to arrive at a product with the desired release characteristics. The materials used to supply the liners for the dressings of the present disclosure can be substantially more rigid than the backing. Liners which can be suitable for use in the adhesive composites of the present disclosure can be made of kraft papers, polyethylene, polypropylene, polyester or composites of any of these materials. The liners can be coated with release agents such as fluorochemicals or silicones. For example, U.S. Pat. No. 4,472,480 (Olson), the disclosure of which is hereby incorporated by reference, describes low surface energy perfluorochemical liners. The liners can be papers, polyolefin films, or polyester films coated with silicone release materials. Examples of commercially available silicone coated release papers are POLYSLIK® silicone release papers available from Loparex (Willowbrook, Ill.).

Suitable skin treatment devices include any device that form pores in the skin or otherwise increase the permeability of skin with respect to transport of a drug. Suitable methods include, but are not limited to, RF ablation, heat ablation, microneedle arrays, electroporation, and sonophoresis. In general, all of these skin treatment methods may be used alone or in any combination with each other.

RF ablation is a method of applying electrodes at respective points on skin of a subject and applying electrical energy between two or more of the electrodes to cause resistive heating and subsequent ablation of the stratum corneum primarily in an area intermediate the respective points. Various techniques for limiting ablation to the stratum corneum are described in U.S. Pat. No. 6,148,232 (Avrahami), the disclosure of which is hereby incorporated by reference, including spacing of the electrodes and monitoring the electrical resistance of skin between adjacent electrodes.

Heat ablation is a method for foil ing micropores in the stratum corneum by heating tissue-bound water above the vapor point with a heat conducting element, so as to enhance transdermal transport of an analyte or active substance. Examples of suitable heat ablation devices may be found in U.S. Pat. Nos. 5,885,211 and 6,173,202 (Eppstein et al), the disclosures of which are hereby incorporated by reference.

Microneedle arrays useful as skin treatment devices may comprise any of a variety of configurations, such as those described in the following patents and patent applications, the disclosures of which are herein incorporated by reference. One embodiment for the microneedle arrays comprises the structures disclosed U.S. Patent Application Publication No. 2005/0261631 (Clarke et al.), which describes microneedles having a truncated tapered shape and a controlled aspect ratio. Still another embodiment for the microneedle arrays comprises the structures disclosed in U.S. Pat. No. 6,091,975 (Daddona et al.) which describes blade-like microprotrusions for piercing the skin. Still another embodiment for the microneedle arrays comprises the structures disclosed in U.S. Pat. No. 6,312,612 (Sherman et al.) which describes tapered structures having a hollow central channel. Still another embodiment for the microneedle arrays comprises the structures disclosed in U.S. Pat. No. 6,379,324 (Gartstein et al.) which describes hollow microneedles having at least one longitudinal blade at the top surface of the tip of the microneedle.

Electroporation may be described as a means for transiently decreasing the electrical resistance of the stratum corneum and increasing the transdermal flux of small molecules by applying an electric field to increase the size of existing pores. U.S. Pat. No. 5,019,034 (Weaver et al.), the disclosure of which is hereby incorporated by reference, describes devices for applying high voltage, short duration electrical pulses on the skin to produce electroporation in order to enhance tissue permeability.

Sonophoresis is a method of application of ultrasound to a small area of skin for enhancing transdermal transport. An example of sonophoresis is disclosed in U.S. Pat. No. 6,234,990 (Rowe et al.), the disclosure of which is hereby incorporated by reference.

Dressings of the present disclosure may be packaged individually in a foil-lined pouch for storage. Other materials, such as multi-laminate polymer films with low moisture and/or oxygen permeability may also be suitable for pouching dressings of the present disclosure. In order to improve storage stability, an optional desiccant and/or oxygen absorber may also be included within a hermetically sealed pouch containing the dressing. Dressings of the present disclosure may alternatively be provided in a rolled or stacked form suitable for use with a dispensing apparatus.

In one embodiment, the length of time that the dressing remains on the skin and in a delivering relationship may be an extended time, for example, from about 12 hours to about 14 days. In certain embodiments, the length of time that the reservoir remains in a delivering relationship can be about 1 day (i.e., daily dosing), about 3 to 4 days (bi-weekly dosing), or about 7 days (weekly dosing).

In another embodiment, the length of time that the dressing remains in a delivering relationship may be relatively short, for example from about 1 minute to about 1 hour, often from about 5 minutes to 40 minutes, and sometimes from about 5 minutes to 20 minutes.

The length of time between treatment of the skin to increase permeability and placement of the drug reservoir in contact with the treated skin area may vary. In one embodiment, this length of time can be kept to a minimum in order to avoid any possibility of the skin barrier reforming through a healing process. The minimum length of time can be generally governed by the time it takes to remove the treatment device from the target skin site, remove the liner and fold the adhesive dressing 110 about the hinge 140, but this time may be less than about 1 minute, less than about 30 seconds, less than about 10 seconds, or less than about 5 seconds. There is no reason, however, that this time cannot be extended to many minutes or hours if so desired. It is generally known that the length of time that the skin will remain increasing permeable after treatment depends on the type of treatment and whether the skin is occluded or not after treatment. In some instances increased permeability can be maintained for up to several days as long as the treated site remains occluded and even in the absence of occlusion the skin may have increased permeability for up to several hours. Thus, if it presented some convenience or clinical benefit, one could treat the site and delay drug delivery by wearing the entire adhesive composite dressing until such time as one desired to begin drug delivery, at which time the liner would be removed and the drug reservoir folded over and placed in contact with the treated skin.

In embodiments, the adhesive composite dressing 100 comprises a backing 113 which can be conformable as described above; a low adhesion coating 115 on a top face of the backing 113; a carrier 112 attached to the top face of the backing 113 over the low adhesion coating 115; a pressure sensitive adhesive 114 on a bottom face of the backing 113; a drug reservoir 116 attached to the pressure sensitive adhesive 114; double coated tape 104 attached to both the backing 113 and carrier 112; release liner 102 attached to the double coated tape 104 and a liner 120 attached to the exposed surface of pressure sensitive adhesive 114.

The carrier 112 can be attached to backing 113 (over low adhesion coating 115) with a heat seal bond. An optional rectangular window portion cut in the carrier 112 can be removed creating a frame 112a and a window 112b exposing a portion of the top face of the backing 113 (See FIG. 2). Frame 112a provides rigidity to the backing 113 after liner 120 is removed. The drug reservoir 116 may be aligned in the center of the frame 112a. As described above, low adhesion coating 115 can be compatible with the heat seal bond between the frame 112a and backing 113. The heat seal bond between the carrier 112 and the backing 113 can be stronger than the bond between the pressure sensitive adhesive 114 and the liner 120. That difference ensures that the backing 113 remains attached to the frame 112 when liner 120 is removed from the adhesive dressing 110. In embodiments, the carrier 112 can be left in its entirety (i.e., the window 112b is removed) and the entire carrier 112 serves to provide rigidity to the backing 113 after liner 120 is removed. The dressing can have a perforation 118 in the adhesive dressing 110 enabling all but the adhesive dressing 110 with drug reservoir 116 to be removed from the patient after application. In use, release liner 102 can be first removed from the adhesive composite dressing 100 leaving the double coated tape 104, carrier 112, adhesive dressing 110, drug reservoir 116, and liner 120 intact. The user can then manipulate the adhesive composite dressing 100 while viewing the target area through the target opening 122 in the liner 120.

Figure 3C:
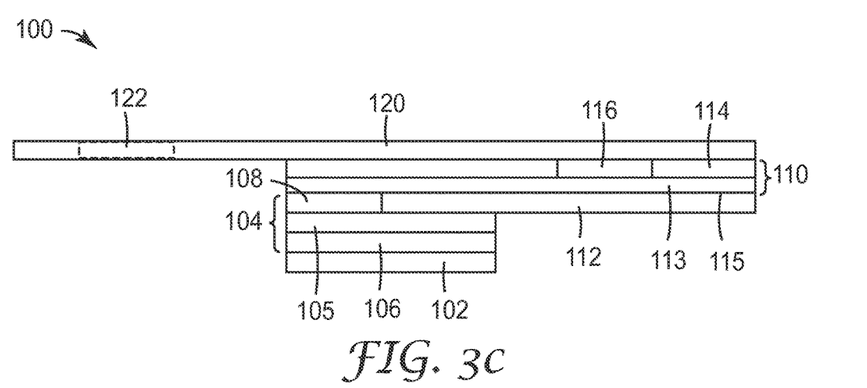
FIG. 3C is a schematic cross-sectional view of a third embodiment of an adhesive composite dressing.

The user attaches the adhesive composite dressing 100 to the skin using the double coated tape 104. The user then treats the skin, as shown in FIG. 4A, through the target opening 122 and removes the liner 120. The user then folds the patch over at the hinge 140 aligning the drug reservoir 116 over the treated skin 132. The hinge 140 can be created at the edge of the carrier 112 as the backing 113 or the adhesive dressing 110 adheres to the double coated tape 104 and the carrier 112 releases from the adhesive layer 108 of the double coated tape 104. During the fold over action (FIG. 4C) a low adhesion coating on the surface of the carrier 112 enables the carrier to release from the adhesive layer 108 of the double coated tape 104 without causing the adhesive composite dressing 100 to fold or the skin-contact adhesive 106 of the double coated tape 104 to detach from the skin. Once the pressure sensitive adhesive 114 contacts the skin, the user removes the carrier 112. Finally, the user removes all but the adhesive dressing 110 and drug reservoir 116 from the skin at the perforation 118. In embodiments, the dressing does not have perforation 118 and the double coated tape 104 remains on the skin along with the adhesive dressing 110 and drug reservoir 116 for the duration of wear. In this embodiment a construction as depicted in FIG. 3C can be used so that the exposed edge of the double coated tape 104 does not have exposed adhesive.

Figure 5:
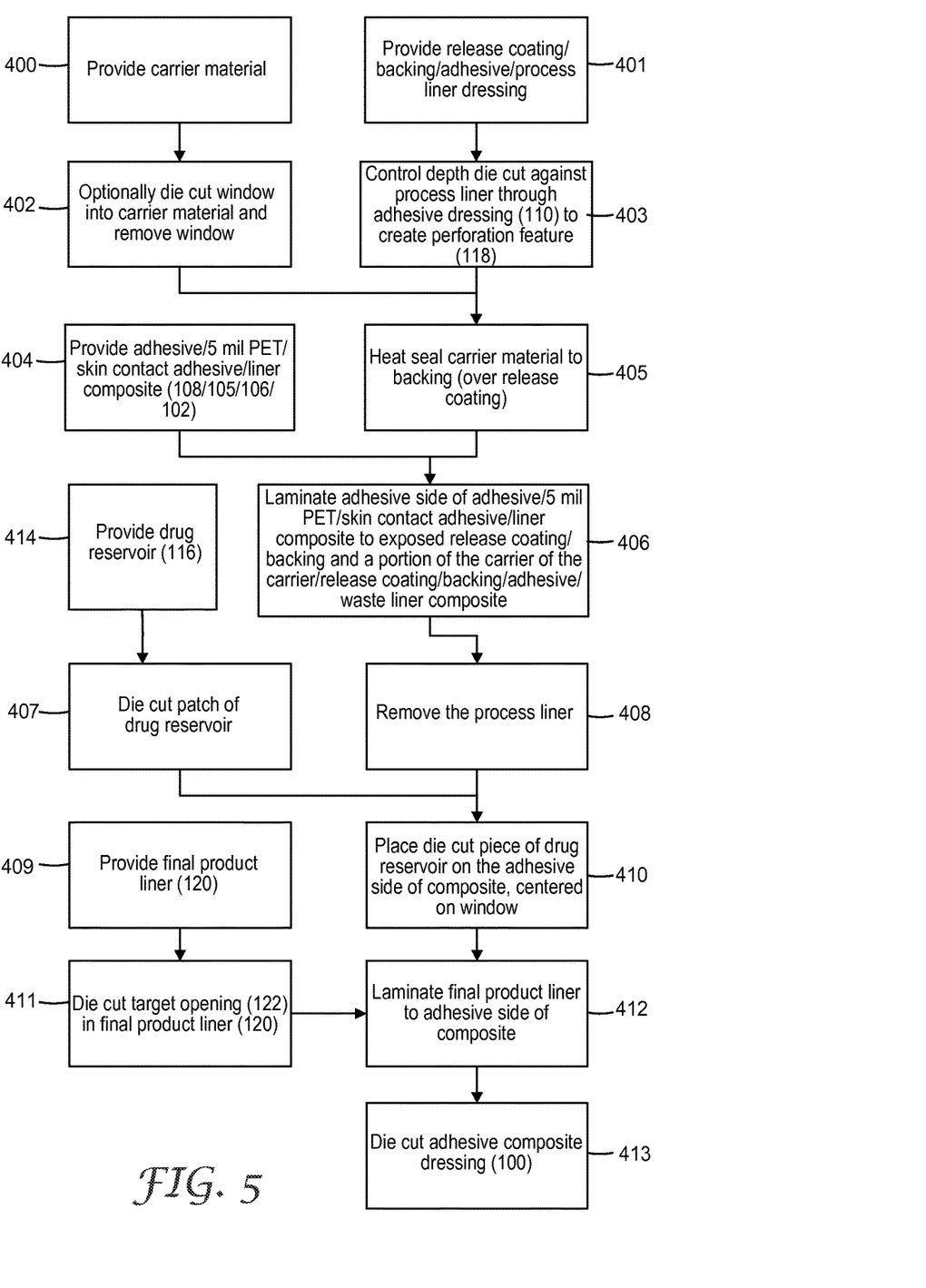
FIG. 5 is a process flow diagram for manufacture of an adhesive composite dressing.
Figure 6:
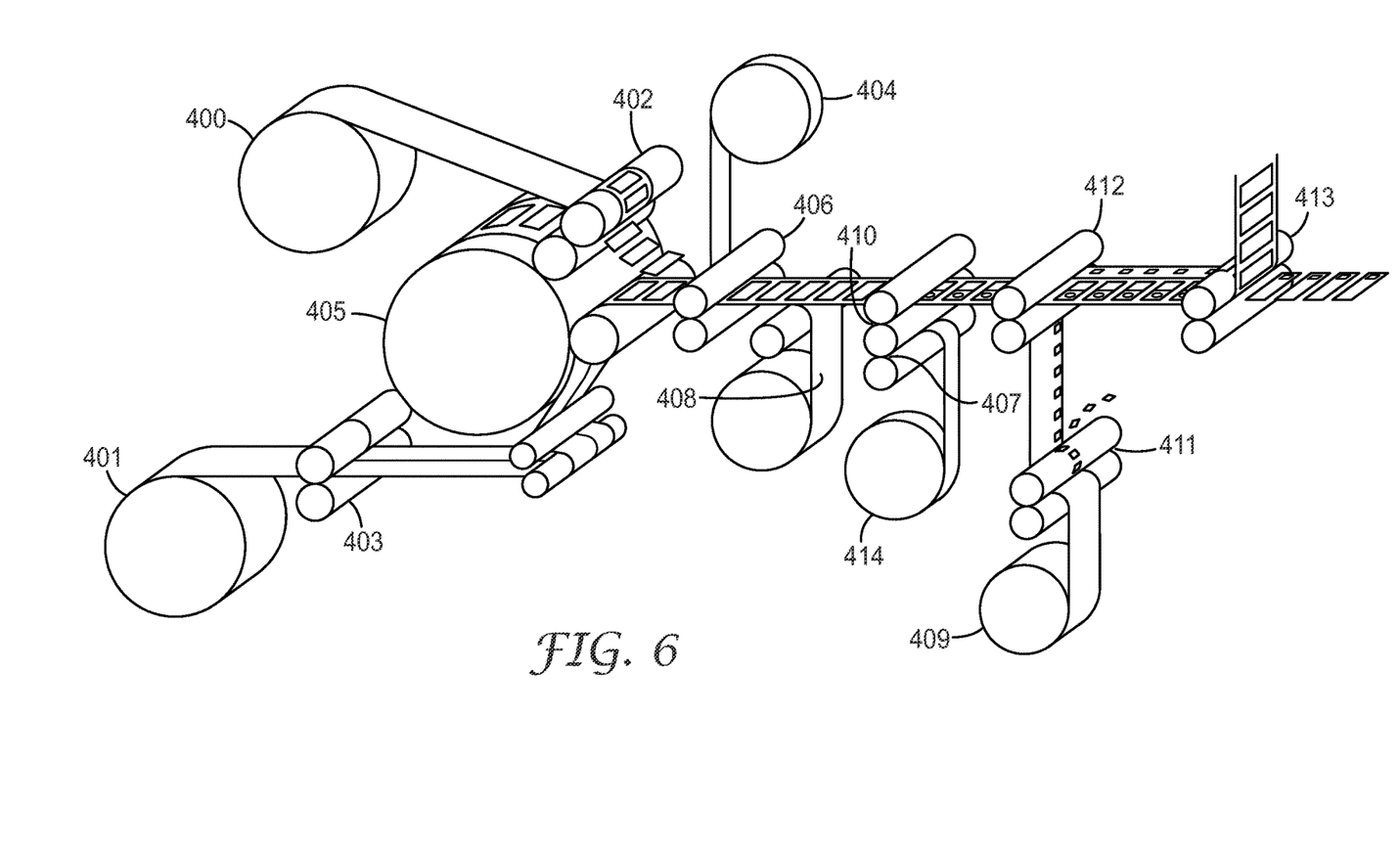
FIG. 6 is a schematic perspective view of an apparatus used for manufacturing adhesive composite dressings.

A method of manufacturing dressings according to the present disclosure is described below with reference to FIGS. 5 and 6. FIG. 5 shows a flow diagram of the process steps. FIG. 6 shows a schematic diagram of web fed rotary processing equipment for producing dressings according to the methods of the present disclosure. The details of designing such equipment will be well known to those skilled in the art. Commercially available rotary web processing equipment including control depth die cut systems useful for practicing the method of the present disclosure can be obtained from, for example, the Mark Andy Company (St. Louis, Mo.) and Bernal Rotary Systems (Troy, Mich.).

In step 401 a web of dressing material formed of a release coating, backing, skin contact adhesive, and process liner is provided. The materials for each component in that web are described above. In step 403, a control depth die cut can be made to fully bisect the backing/skin contact adhesive portion of the web, thus forming the perforation 118, while leaving the process liner fully intact. The intact process liner maintains the integrity of the dressing material. In embodiments, the control depth die cut can be accomplished using rotary die cutting equipment, which equipment is well known to those skilled in the art.

In step 400 a carrier material is provided and optionally die cut in step 402 to form the window which lies in the center of the carrier. This die cutting can be accomplished using rotary die cutting equipment. After the windows have been die cut in the carrier material, they can also be removed in step 402. Removal of the windows defines the inner edge of the frame of carrier material which is located around the perimeter of each of the adhesive dressings.

The windows die cut into the carrier material can be removed using a number of methods known to those skilled in the art. Those methods could include the use of vacuum, air pressure, gravity, and nip rolls having a small diameter which cause the windows to be removed from the framed carrier material.

As discussed above, the carrier material forming the window is removed and is thus not heat sealed to the backing as is the remainder of the carrier material making up the frame of each dressing. After the die cutting and window removal step 402 is completed, the carrier material (with windows removed) can be heat sealed in step 405 to the top face of the backing over the low adhesion coating. The hinge 140 edge of the carrier 112 can be precisely aligned with the crossweb datum of the dressing using web guidance equipment and fixtures known to those skilled in the art. Alternatively, a weed may be slit from the carrier 112 immediately prior lamination to create a precisely located hinge 140 edge with respect to the cross-web datum of the dressing. A portion of the release coated backing can be not covered by the carrier and this portion will serve to define one side of the hinge.

In step 404, a double sided adhesive tape comprising an adhesive layer 108, a polyester film, a skin-contact adhesive, and a liner is provided. In step 406, the adhesive layer 108 of the double sided tape can be laminated to the exposed release coated backing, as well as to a portion of the carrier.

Next, the waste liner can be removed from the composite in step 408, exposing the pressure sensitive adhesive 106. Drug reservoir 116 patches are provided in step 414, die cut in step 407, and precisely placed in alignment with the frame 112a in step 410 using a number of methods known to those skilled in the art. Those methods could include the use of vacuum, air pressure, side lay adjustment of the die station, sensors, controllers and servo controlled drives to accurately place the medicament with respect to the crossweb datum of the dressing and downweb registration of the frame.

A final product liner 120 is provided in step 409 and a target opening 122 can be die cut in step 411 in the liner. Precise alignment of the target opening to the crossweb datum and downweb frame repeat is similar to methods employed for accurate medicament placement. Target opening 122 waste can be removed in a fashion similar to window waste removal. The liner 120 can be then laminated to the pressure sensitive adhesive 114 of the composite dressing in step 412.

Finally, in step 413 the web can be directed into a rotary die sheeting station which cuts adhesive composite dressings out of the web and pulls the weed or waste material away for disposal. The individual adhesive composite dressings can be fed directly into a packaging station which places the dressings in their final primary package.

What is claimed is:

1. An adhesive composite dressing comprising:
   an anchor member comprising a first skin-contact adhesive;
   a target member comprising an opening adapted to enable skin treatment;
   a folding member comprising a drug reservoir and a second skin-contact adhesive, wherein the folding member is attached to the anchor member through a hinge defined by a line of attachment that is not contiguous with an edge of the anchor member; and
   an impermeable barrier between the drug reservoir and the second skin-contact adhesive.

2. The adhesive composite dressing of claim 1 wherein the folding member is attached to the anchor member by an adhesive layer.

3. The adhesive composite dressing of claim 1 further comprising a support layer releasably attached to the folding member on a side opposed to the second skin-contact adhesive.

4. The adhesive composite dressing of claim 1 wherein the drug reservoir and the target member opening are positioned opposed to each other and equidistant from the hinge so that the drug reservoir may come into alignment with a treated area of skin when the folding member is folded so as to be adjacent to the treated area of skin.

5. An adhesive composite dressing of claim 1, wherein the adhesive composite dressing is adapted to be connected to a skin treatment device.

6. The adhesive composite dressing of claim 5 wherein the dressing is adapted to be releasably connected to the skin treatment device by an adhesive, mechanically, or by magnetic force.

7. The adhesive composite dressing of claim 1 wherein the drug reservoir comprises a drug selected from the group consisting of proteins, peptides, nucleotide sequences, monoclonal antibodies, vaccines, polysaccharides, and antibiotics.

8. The adhesive composite dressing of claim 1 wherein the dressing is provided within a hermetically sealed pouch.

9. A kit comprising:
   an adhesive composite dressing of claim 1; and
   a skin treatment device.

10. The kit of claim 9 wherein the adhesive composite dressing is releasably attached to the skin treatment device.

11. A method of applying a drug reservoir to a treated area of skin with a patch comprising an anchor member, a target member, and a folding member, the folding member comprising the drug reservoir and being attached to the anchor portion through a hinge defined by a line of attachment that is not contiguous with an edge of the anchor member, the target member comprising an opening adapted to enable skin treatment, the method comprising:
   attaching the anchor member of the patch to a non-treated area of skin,
   treating the area of skin left exposed by the target opening with a treatment method that increases the permeability of the skin,
   rotating the folding member around the hinge so that at least a portion of the folding member adheres to the skin and so that the drug reservoir contacts the treated area of skin and
   removing the anchor member from the skin while leaving the drug reservoir in contact with the treated area of skin.

12. The method of claim 11 wherein the skin is treated with a skin treatment device selected from the group consisting of an RF ablation device, a heat ablation device, and a microneedle array.

13. The method of claim 11 wherein the increased permeability of the skin is with respect to pharmaceutically active agents.

14. The method of claim 11 wherein the treatment method forms a plurality of pores in the skin.

* * * * *